United States Patent [19]
Alexander

[11] Patent Number: 5,964,735
[45] Date of Patent: Oct. 12, 1999

[54] FINE NEEDLE ASPIRATION SAFETY SYRINGE

[75] Inventor: Gary E. Alexander, Baton Rouge, La.

[73] Assignee: Medisys Technologies, Inc., Baton Rouge, La.

[21] Appl. No.: 08/886,393

[22] Filed: Jul. 1, 1997

[51] Int. Cl.[6] .................................................. A61M 5/00
[52] U.S. Cl. .......................................... 604/195; 604/110
[58] Field of Search .................................. 604/187, 110, 604/195, 198, 192, 263, 272

[56] References Cited

U.S. PATENT DOCUMENTS

| | | | |
|---|---|---|---|
| 3,094,122 | 6/1963 | Gauthier et al. | 128/221 |
| 4,026,287 | 5/1977 | Haller | 128/215 |
| 4,197,846 | 4/1980 | Bucalo | 128/218 |
| 4,425,120 | 1/1984 | Sampson et al. | 604/198 |
| 4,464,171 | 8/1984 | Garwin | 604/53 |
| 4,581,021 | 4/1986 | Landau et al. | 604/212 |
| 4,636,202 | 1/1987 | Lowin et al. | 604/236 |
| 4,702,738 | 10/1987 | Spencer | 604/198 |
| 4,737,150 | 4/1988 | Baeumle et al. | 604/198 |
| 4,846,785 | 7/1989 | Cassou et al. | 600/34 |
| 4,846,799 | 7/1989 | Tanaka et al. | 604/158 |
| 4,850,996 | 7/1989 | Cree | 604/198 |
| 4,863,434 | 9/1989 | Bayless | 604/198 |
| 4,863,435 | 9/1989 | Sturman et al. | 604/198 |
| 4,874,382 | 10/1989 | Lindemann et al. | 604/195 |
| 4,875,896 | 10/1989 | Kurtz | 604/187 |
| 4,883,471 | 11/1989 | Braginetz et al. | 604/195 |
| 4,883,472 | 11/1989 | Michel | 604/208 |
| 4,894,055 | 1/1990 | Sudnak | 604/198 |
| 4,909,791 | 3/1990 | Norelli | 604/192 |
| 4,909,792 | 3/1990 | Norelli | 604/192 |
| 4,923,445 | 5/1990 | Ryan | 604/195 |
| 4,929,237 | 5/1990 | Medway | 604/198 |
| 4,935,014 | 6/1990 | Haber | 604/195 |
| 4,935,016 | 6/1990 | Deleo | 604/198 |
| 4,936,830 | 6/1990 | Verlier | 604/110 |
| 4,944,723 | 7/1990 | Haber et al. | 604/110 |
| 4,966,592 | 10/1990 | Burns et al. | 604/198 |
| 4,966,593 | 10/1990 | Lennox | 604/198 |
| 4,969,877 | 11/1990 | Kornberg | 604/195 |
| 4,973,316 | 11/1990 | Dysarz | 604/195 |
| 4,973,317 | 11/1990 | Bobrove | 604/198 |
| 4,976,701 | 12/1990 | Ejlersen et al. | 604/192 |
| 4,982,842 | 1/1991 | Hollister | 206/365 |
| 4,986,819 | 1/1991 | Sobel | 604/198 |
| 4,994,041 | 2/1991 | Dombrowski et al. | 604/164 |
| 5,015,240 | 5/1991 | Soproni et al. | 604/192 |
| 5,024,659 | 6/1991 | Sjostrom | 604/272 |
| 5,026,353 | 6/1991 | Bartman | 604/192 |
| 5,032,117 | 7/1991 | Motta | 604/88 |
| 5,051,109 | 9/1991 | Simon | 604/263 |
| 5,067,942 | 11/1991 | Jaffe et al. | 604/110 |
| 5,092,851 | 3/1992 | Ragner | 604/192 |

(List continued on next page.)

FOREIGN PATENT DOCUMENTS

WO 89/08468  9/1989  WIPO.

*Primary Examiner*—John D. Yasko
*Attorney, Agent, or Firm*—Roy, Kiesel & Tucker, PLC

[57] ABSTRACT

The invention comprises a needle aspiration safety syringe having a barrel, a plunger, a retractable needle, and a delayed engagement mechanism. The needle is functionally connected to the plunger by the delayed engagement mechanism such that when the plunger is retracted from an initial extended position, the needle does not retract immediately. The needle provides passage into the fluid receiving cavity, such that retraction of the plunger causes tissue fluid to flow from a target tissue through the needle and into the fluid receiving cavity. Further retraction of the plunger causes the delayed engagement mechanism to engage, whereupon the needle can be withdrawn completely into the fluid receiving cavity, such that the sharp end of the needle is no longer exposed. After the needle withdraws completely into the fluid receiving cavity, the needle cannot exit the fluid receiving cavity, such that the sharp end of the needle poses no danger of sticking a user or patient. Fluids can be stored in the fluid receiving cavity, and can be discharged through a port by depressing the plunger. When the plunger is depressed to discharge collected tissue fluid, the needle deforms inside the barrel.

82 Claims, 3 Drawing Sheets

U.S. PATENT DOCUMENTS

| | | | |
|---|---|---|---|
| 5,092,852 | 3/1992 | Poling | 604/192 |
| 5,098,401 | 3/1992 | De Lange | 604/192 |
| 5,104,384 | 4/1992 | Parry | 604/192 |
| 5,122,123 | 6/1992 | Vaillancourt | 604/192 |
| 5,135,507 | 8/1992 | Haber et al. | 604/187 |
| 5,151,088 | 9/1992 | Allison et al. | 604/192 |
| 5,205,825 | 4/1993 | Allison | 604/110 |
| 5,205,826 | 4/1993 | Chen | 604/195 |
| 5,282,792 | 2/1994 | Imbert | 604/187 |
| 5,300,038 | 4/1994 | Haber et al. | 604/187 |
| 5,306,258 | 4/1994 | de la Fuente | 604/198 |
| 5,314,503 | 5/1994 | Bobrove et al. | 604/164 |
| 5,342,320 | 8/1994 | Cameron | 604/192 |
| 5,370,628 | 12/1994 | Allison | 604/192 |
| 5,383,851 | 1/1995 | McKinnon, Jr. et al. | 604/68 |
| 5,385,555 | 1/1995 | Hausser | 604/192 |
| 5,503,627 | 4/1996 | McKinnon et al. | 604/72 |
| 5,520,639 | 5/1996 | Peterson et al. | 604/68 |
| 5,540,660 | 7/1996 | Jenson | 604/195 |

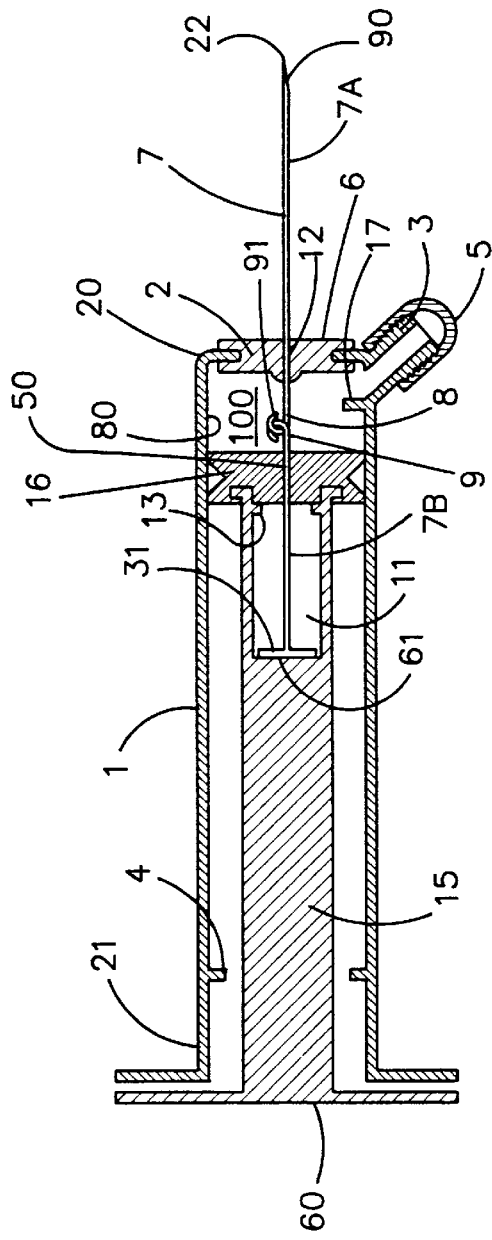
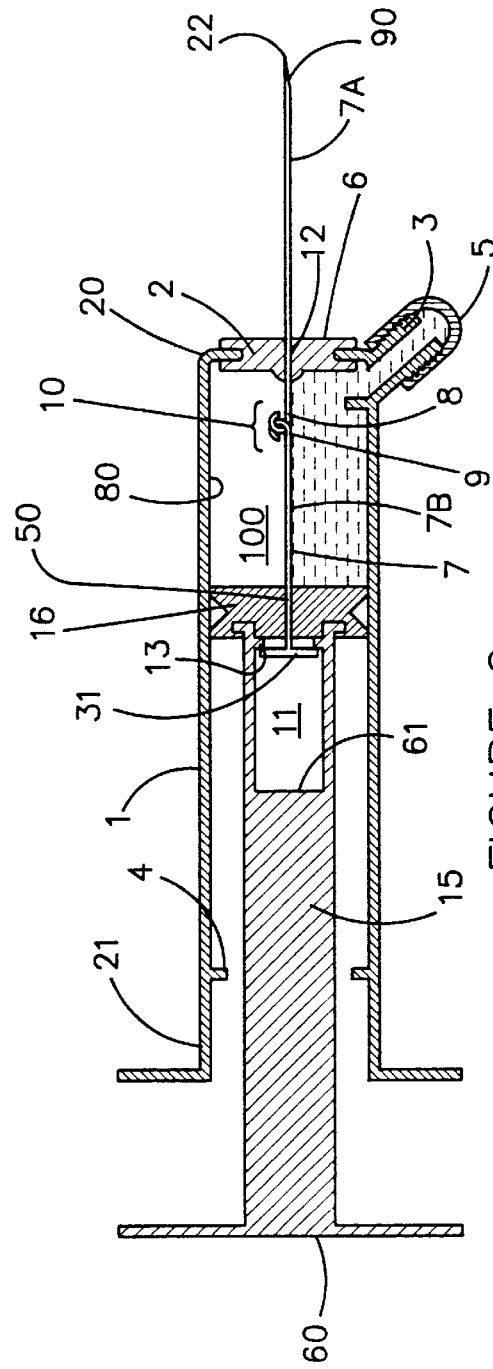
FIGURE 1
FIGURE 2

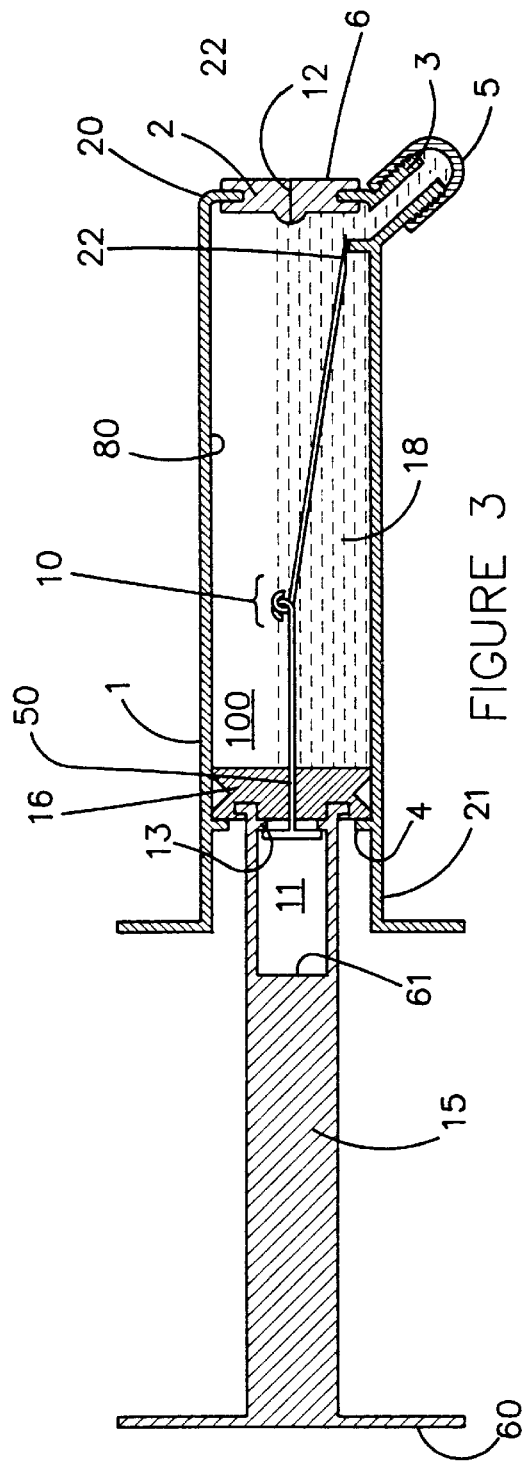
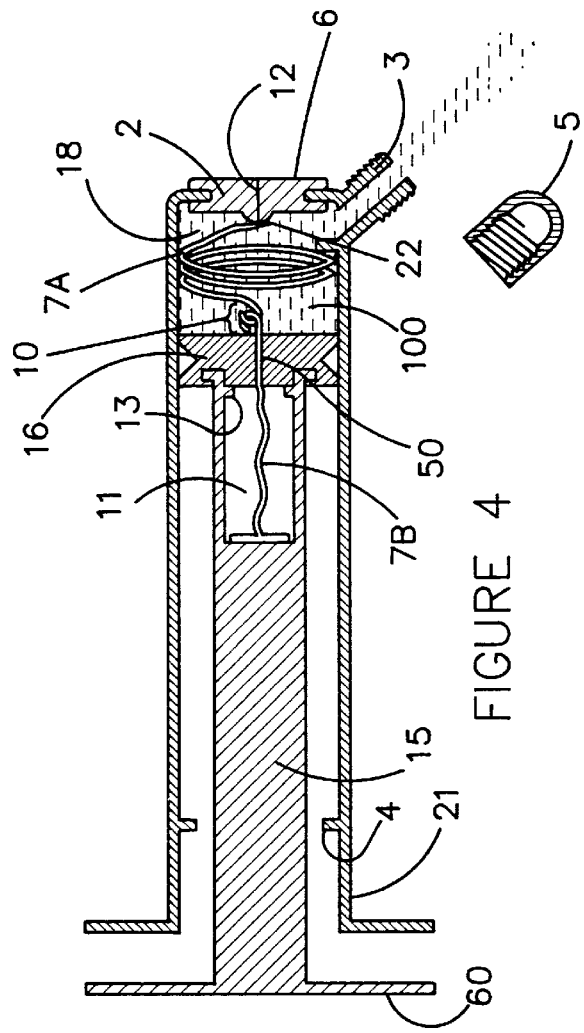

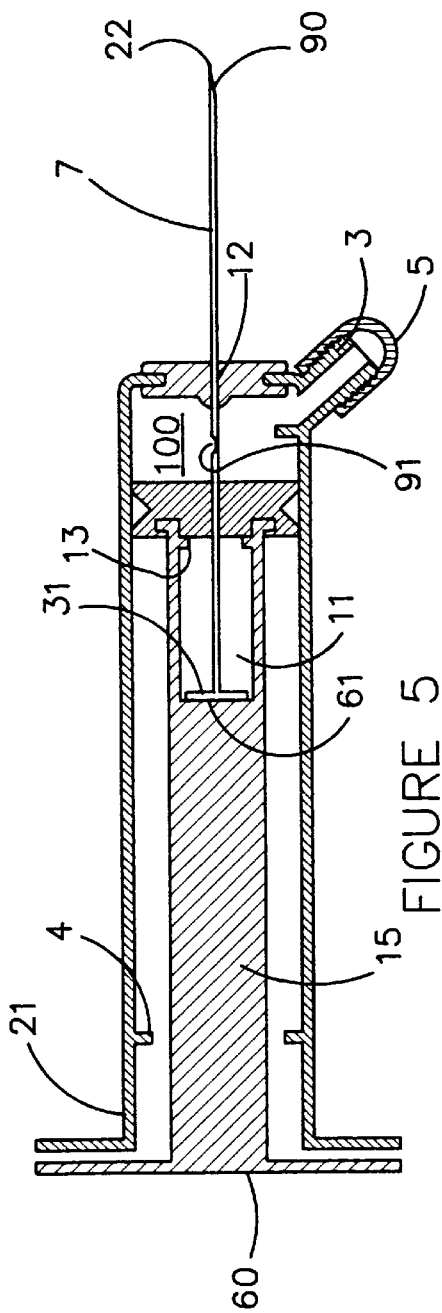
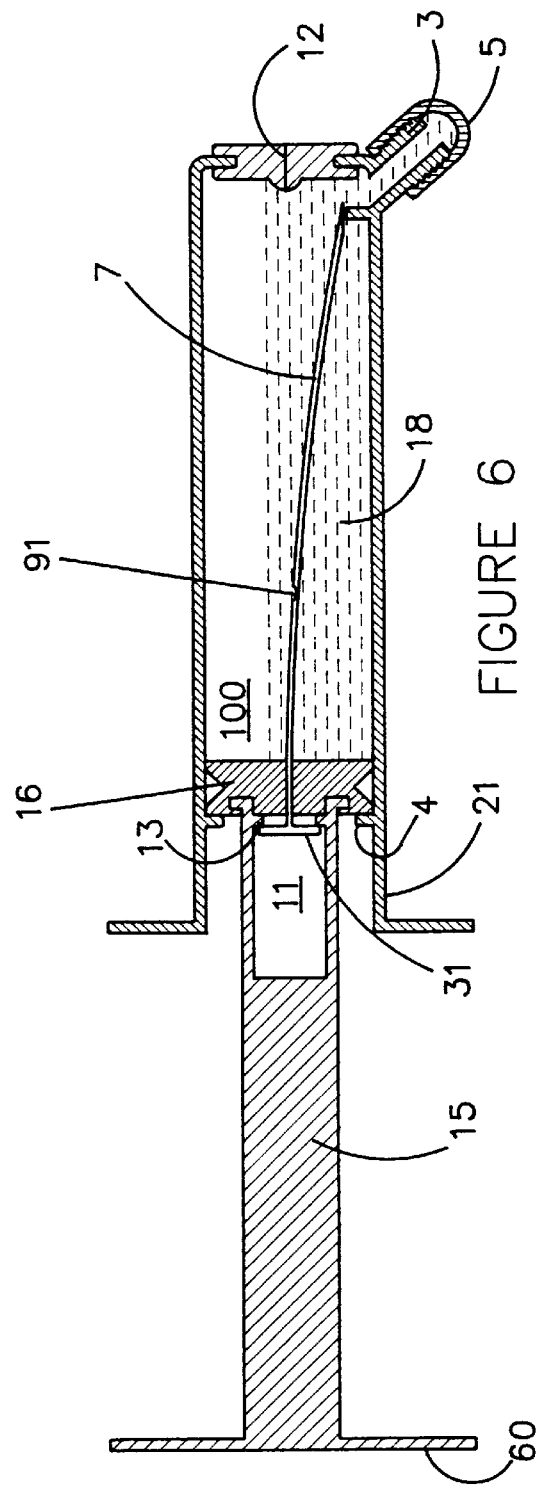

FINE NEEDLE ASPIRATION SAFETY SYRINGE

FIELD OF THE INVENTION

The present invention relates to needle safety syringes in general, and to aspirations or biopsies using needles in particular.

BACKGROUND OF THE INVENTION

The risk of contracting diseases such as HIV or hepatitis from accidental sticks with dirty needles is a potentially deadly hazard for medical professionals. Although many syringe designs have been created to avoid or minimize the risk of dirty needle sticks, few if any of these designs have been directed to syringes for collecting aspirated matter.

There are more than fifty diseases in which fine needle aspirations or biopsies are used in the diagnostic process to collect body fluids and matter suspended in body fluids. Some of these aspirations involve detection of a carcinoma, such as with suspected breast or prostate cancer. In detecting carcinomas, fine needles of 25 to 30-gauge are used in order to reduce the risk of needle tracking, which occurs when cancerous cells contained in a lesion track the needle path upon withdrawal, thereby possibly creating an artificial metastasis. Sheaths, which protect the operator from inadvertent self puncture with contaminated needles in intramuscular injection and other sharps procedures, cannot be used to detect carcinomas because they result in an increased diameter of the needle path, thereby facilitating needle tracking.

Needle aspirations are typically performed by physicians. However, because most needle puncture procedures are performed by nurses, practically all research and development of sharps safety procedures have been directed toward these procedures, leaving the needle biopsy physician unprotected. The problems associated with needle tracking, and the comparatively small number of fine needle aspirations, has resulted in little or no improvement in safety factors related to needle biopsy procedures. While relatively small in number in comparison to the other sharps procedures combined, millions of needle biopsy procedures are performed every year. Consequently, there is a very real need for needle aspiration safety syringes for avoiding dirty needle sticks. Accordingly, a safety syringe that meets the following objectives is disclosed.

SUMMARY OF THE INVENTION

The invention comprises a needle aspiration safety syringe having a barrel, a plunger, a needle, and a delayed engagement mechanism. The needle is functionally connected to the plunger by the delayed engagement mechanism such that when the plunger is retracted from an initial extended position, the needle does not retract immediately. Thus, upon insertion of the needle into a target tissue in the patient, the plunger may be retracted without retracting the needle. Retraction of the plunger creates a vacuum within a fluid receiving cavity in the barrel. The needle provides passage into the fluid receiving cavity, such that retraction of the plunger causes tissue fluid to flow from the target tissue through the needle and into the fluid receiving cavity.

Once the desired amount of fluid has been collected, the syringe may be removed from the body of the patient. Further retraction of the plunger causes the delayed engagement mechanism to engage, whereupon the needle begins to withdraw into the fluid receiving cavity. Continued retraction of the plunger causes the needle to withdraw completely into the fluid receiving cavity, such that the sharp end of the needle is no longer exposed. After the needle withdraws completely into the fluid receiving cavity, the needle cannot exit the fluid receiving cavity, such that the sharp end of the needle poses no danger of sticking a user or patient.

Fluids can be stored in the fluid receiving cavity until discharge is desired. The barrel has a port which provides a passage from the fluid receiving cavity. The port is sealed during fluid collection. Collected fluids can be discharged through the port by removing the seal and depressing the plunger. When the plunger is depressed after the sharp end of the needle has withdrawn into the fluid receiving cavity, the needle deforms within the fluid receiving cavity, thereby preventing both reuse and accidental sticks without interfering with the use of the plunger to discharge fluids from the syringe. Use of a needle entry barrier prevents the sharp end of the needle from exiting through the port when the plunger is depressed.

OBJECTS OF THE INVENTION

It is therefore an object of the invention to reduce the risk of dirty needle stick to physicians during the performance of needle aspirations.

It is an object of the invention to reduce handling steps with aspirated matter in order to reduce contact with blood or other fluid borne pathogens, such as AIDS or hepatitis.

It is an object of the invention to eliminate the use, cost, and handling of vials used to transport aspirate matter.

It is an object of the invention to help prevent the transmission of AIDS and other diseases through accidental sticks with contaminated needles.

It is an object of the invention to provide a needle aspiration safety syringe which minimizes the chances of an accidental stick with a contaminated needle.

It is an object of the invention to provide a needle aspiration safety syringe capable of collecting blood and other fluids.

It is an object of the invention to provide a needle safety syringe in which the needle can be readily covered after removal from a patient.

It is yet another object of the invention to provide a needle aspiration safety syringe whose contents may be expelled without exposing the needle.

It is still another object of the invention to provide a needle safety syringe which is designed to prevent reuse.

These and other objects and advantages of the invention will become apparent from the following description of the preferred embodiments of the invention.

BRIEF DESCRIPTION OF THE DRAWINGS

FIG. 1 is a cross-sectional side view of a preferred embodiment showing a needle in an extended position.

FIG. 2 is a cross-sectional side view of a preferred embodiment showing a needle in a partially retracted position, such that engagement has occurred between the plunger and an engagement end of the two-part needle.

FIG. 3 is a cross-sectional side view of a preferred embodiment showing a needle in a fully retracted position, with the sharp end of the needle withdrawn into the fluid receiving cavity.

FIG. 4 is a cross-sectional side view of a preferred embodiment showing a needle in an extended position after the sharp end of the needle has withdrawn into the fluid receiving cavity, further showing deformation of the needle within the fluid receiving cavity and the discharge of collected aspirated matter through an open port.

FIG. 5 is a cross-sectional side view of a preferred embodiment showing a needle in an extended position.

FIG. 6 is a cross-sectional side view of a preferred embodiment showing a needle in a fully retracted position, with the sharp end of the needle withdrawn into the fluid receiving cavity.

DETAILED DESCRIPTION OF THE PREFERRED EMBODIMENTS OF THE INVENTION

As shown in FIG. 1, the needle aspiration safety syringe comprises a substantially hollow barrel 1 having a needle end 20, a plunger end 21, and an interior wall 80 extending between needle end 20 and plunger end 21. Needle end 20 is sealed, with the exception of a friction fit needle aperture 12. Friction fit needle aperture 12 is preferably centered in needle end 20. Needle end 20 can have an oversized opening 2 sealed with an oversized seal or grommet 6, in which case friction fit needle aperture 12 extends through oversized seal 6. In a preferred embodiment, calibrated measurement lines are marked on barrel 1, and barrel 1 is made of transparent or translucent plastic.

As shown in FIG. 1, a plunger 15 is positioned in hollow barrel 1. Plunger 15 has a thumb end 60 and a washer end 16. Thumb end 60 extends or projects from plunger end 21 of barrel 1. Thumb end 60 is configured such that it can be readily pulled or pushed by the thumb, fingers, or hand of a user. Washer end 16 of the plunger is sized and configured to engage interior wall 80 so that a substantially fluid tight seal is created between washer end 16 and interior wall 80 of barrel 1. In a preferred embodiment, washer end 16 is made of or covered with rubber while plunger 15 is made of plastic. A rear travel detente 4 is positioned on plunger end 21. Rear travel detente 4 prevents washer end 16 of plunger 15 from withdrawing from plunger end 21 of barrel 1 when plunger 15 is fully retracted, as shown in FIGS. 3 and 6.

Together, washer end 16 of plunger 15, needle end 20 of barrel 1, and interior wall 80 between washer end 16 and needle end 20, form or define a fluid receiving cavity 100. Retraction of plunger 15 within barrel 1, from an extended position in which washer end 16 is positioned near the needle end 20, to retracted positions in which washer end 16 moves away from needle end 20 toward rear travel detente 4, increases the volume of the fluid receiving cavity 100, thereby creating a vacuum in fluid receiving cavity 100. Likewise, depressing plunger 15 to an extended position, with washer end 16 moving toward needle end 20, creates internal pressure in fluid receiving cavity 100. This internal pressure can be used to expel collected aspirated matter 18 from fluid collection cavity 100, particularly through a port 3, as will be described.

As shown in FIG. 1, washer end 16 of plunger 15 has a plunger cavity 11 therein for receiving an engagement end 31 of a retractable needle 7, as will be described. An engagement means 13, such as a forward travel detente 13, is positioned in plunger cavity 11. As shown in FIGS. 2, 3, and 6, engagement means 13 engages engagement end 31 of retractable needle 7 upon retraction, such that retractable needle 7 can be pulled by plunger 15, as will be described. Engagement means 13 is positioned and configured such that plunger 15 can be partially retracted without engaging engagement end 31 or retracting retractable needle 7. Once engagement means 13 engages engagement member 31, further retraction causes retractable needle 7 to retract into fluid receiving cavity 100.

A hole 50 extends through washer end 16 of plunger 15. Retractable needle 7, or engagement member 7B of a two-part retractable needle 7, extends through hole 50, such that engagement end 31 is positioned within plunger cavity 11. In the preferred embodiment, hole 50 is slightly larger than retractable needle 7 or the engagement member 7B, such that retractable needle 7 or engagement member 7B is slidably disposed within hole 50. However, hole 50 can be as large as the width or diameter of plunger cavity 11, provided an engagement means 13, such as a forward travel detente 13, is positioned in plunger cavity 11 to prevent engagement end 31 from withdrawing from plunger cavity 11 during retraction of plunger 15. Plunger cavity 11 may be fluidly connected to fluid receiving cavity 100, in which case plunger cavity 11 should be sealed so as not to destroy or interfere with the vacuum and compression features of fluid receiving cavity 100. Plunger cavity 11 has a rear wall 61 which serves to propel and deform retractable needle 7 or engagement member 7B when plunger 15 is depressed to return plunger 15 to an extended position.

As shown in FIGS. 1–4, a preferred embodiment of the invention comprises a two part retractable needle 7 having a pivot 10. As shown in FIGS. 5–6, another preferred embodiment of the invention comprises a one part retractable needle 7. Regardless of which configuration of retractable needle 7 is used, retractable needle 7 and needle member 7A of two-part retractable needle 7 are hollow, and contain a first needle opening 90 on or proximate sharp end 22 which provides fluid passage into the hollow center of retractable needle 7 or needle member 7A. One or more second needle openings 91 may be provided to provide fluid passage into the hollow center. Second needle openings 91 should preferably be positioned such that fluid flowing through retractable needle 7 or needle member 7A may enter fluid receiving cavity 100. Preferably, the combined surface area of second needle openings 91 should at least equal the surface area of first needle opening 90.

The two-part retractable needle 7 shown in FIGS. 1–4 consists of a needle member 7A, an engagement member 7B, and a pivot 10 between needle member 7A and engagement member 7B. Needle member 7A is preferably made of stainless steel. Needle member 7A has a sharp end 22 and a pivot end 8. Because retractable needle 7 is designed for aspiration procedures, retractable needle 7 preferably has a small diameter, such as is found in needles of about 25 to about 30-gauge. Needles come in twenty-five standard gauges, where gauge is a measure of the external diameter of the needle. Standard needles range from 30 gauge, which has an external diameter of $12/1000$ of an inch, to 6 gauge, which has an external diameter of $200/1000$ of an inch. Although the safety syringe may be used with any needle which is capable of deforming within the fluid receiving cavity, needles in the smaller end of the standard needle range are expected to be used most often in aspiration procedures, particularly where there is a risk of needle tracking. If it is desirable to use a larger needle, the needle can be scored such that it will break and deform within the fluid receiving cavity. Needle member 7A can have a larger diameter on pivot end 8, provided that sharp end 22 has a length of a diameter sufficient for carrying out the desired aspiration procedure.

Engagement member 7B of retractable needle 7 has an engagement end 31 and a tractor end 9. In a preferred embodiment, engagement member 7B is substantially flat. Tractor end 9 of engagement member 7B is pivotally engaged with pivot end 8 of needle member 7A, forming pivot 10. Pivot 10 can be formed in any of numerous configurations. For example, tractor end 9 can be provided with a hole and pivot end 8 with a hook which engages the hole of tractor end 9. Alternatively, tractor end 9 can be provided with a hook and pivot end 8 with a hole which engages the hook of tractor end 9. Similarly, both tractor end 9 and pivot end 8 can be provided with hooks, or holes, which engage each other. A third link can also be provided between the needle member 7A and engagement member 7B of retractable needle 7. Regardless of which configuration is used to form pivot 10, pivot 10 provides a point or range of points about which sharp end 22 can pivot when sharp end 22 is retracted through friction fit needle aperture 12, as will be described.

In an initial extended position, sharp end 22 of needle member 7A extends through friction fit needle aperture 12, as shown in FIG. 1. As mentioned above, engagement end 31 of engagement member 7B is slidably disposed in plunger cavity 11, such engagement end 31 engages engagement means 13 from after partial retraction of the plunger 15 from the extended position. As mentioned above, needle member 7A provides a passage into fluid receiving cavity 100, whereby retraction of plunger 15 creates a vacuum in fluid receiving cavity 100 for drawing aspirated matter 18 through retractable needle 7 into fluid receiving cavity 100.

As shown in FIG. 2, during retraction of plunger 15, engagement means 13 eventually engages engagement end 31 of engagement member 7B. When retractable needle 7 is retracted further after engagement of engagement end 31 by engagement member 7B, needle member 7A begins to withdraw through friction fit needle aperture 12. Upon further retraction, sharp end 22 of needle member 7A withdraws completely through friction fit needle aperture 12 into fluid receiving cavity 100, as shown in FIG. 3. When sharp end 22 of needle member 7A withdraws completely through friction fit needle aperture 12 into fluid receiving cavity 100, needle member 7A pivots about pivot 10, such that sharp end 22 of needle member 7A falls out of alignment with friction fit needle aperture 12. Friction fit needle aperture 12 is self sealing, such that when needle member 7A withdraws from friction fit needle aperture 12, aspirated matter 18 cannot exit through the friction fit needle aperture 12. Thus, needle end 20 of barrel 1 and fluid receiving cavity 100 are substantially fluid tight when retractable needle 7 is fully withdrawn into barrel 1. Because needle end 20 of barrel 1 and fluid receiving cavity 100 are substantially fluid tight, the syringe is in a safe condition for labeling, transport, or storage, without the necessity of transferring aspirated matter to vials or other transport containers.

As shown in FIG. 4, needle member 7A is preferably very thin, such that it will readily deform or crumple within fluid receiving cavity 100 when plunger 15 is returned toward an extended position after sharp end 22 of needle member 7A has withdrawn through friction fit needle aperture 12. As shown in FIG. 4, the engagement member can also be configured to deform when plunger 15 is returned toward an extended position after sharp end 22 of needle member 7A has withdrawn through friction fit needle aperture 12. Needle member 7A can also be scored to facilitate bending and breaking of needle member 7A within fluid receiving cavity 100 when plunger 15 is returned toward an extended position after sharp end 22 of needle member 7A has withdrawn through friction fit needle aperture 12. For example, needle member 7A can be scored 270 degrees at ½ inch intervals to facilitate bending and breaking upon return of plunger 15 toward an extended position. For most aspiration sized needles, scoring is not expected to be necessary.

As shown in FIG. 4, engagement member 7B may crumple or deform in a manner similar to needle member 7A, particularly when plunger 15 is depressed fully toward needle end 20 of barrel 1.

The one-part retractable needle 7 shown in FIGS. 5 and 6 has a sharp end 22 and an engagement end 31. Retractable needle 7 is preferably made of stainless steel. Because retractable needle 7 is designed for aspiration procedures, the needle has a small diameter, such as is found in needles of about 25 to about 30 gauge, as discussed above. Retractable needle 7 can have a larger diameter on the engagement end 31, provided that sharp end 22 has a length of a diameter sufficient for carrying out the desired aspiration procedure. In an initial extended position, sharp end 22 of needle 7 extends through friction fit needle aperture 12 of needle end 20 of barrel 1, as shown in FIG. 5. As mentioned above, engagement end 31 of retractable needle 7 is slidably disposed in plunger cavity 11, such that engagement end 31 can be engaged by engagement means 13 upon partial retraction of plunger 15. As mentioned above, retractable needle 7 provides a passage into fluid receiving cavity 100, whereby retraction of plunger 15 creates a vacuum in fluid receiving cavity 100 for drawing aspirated matter 18 through retractable needle 7 into fluid receiving cavity 100.

As shown in FIG. 6, during retraction of plunger 15, engagement means 13 eventually engages engagement end 31 of retractable needle 7. When retractable needle 7 is retracted further after engagement of engagement end 31 by engagement member 7B, retractable needle 7 begins to withdraw through friction fit needle aperture 12. Upon further retraction, sharp end 22 of retractable needle 7 withdraws completely through friction fit needle aperture 12 into fluid receiving cavity 100, as shown in FIG. 6. Friction fit needle aperture 12 is self sealing, such that when the retractable needle 7 withdraws from friction fit needle aperture 12, aspirated matter 18 cannot exit through friction fit needle aperture 12. Thus, needle end 20 of barrel 1 and fluid receiving cavity 100 are substantially fluid tight when retractable needle 7 is fully withdrawn into barrel 1. Because needle end 20 of barrel 1 and fluid receiving cavity 100 are substantially fluid tight, the syringe is in a safe condition for labeling, transport, or storage, without the necessity of transferring aspirated matter to vials or other transport containers.

As shown in FIG. 6, retractable needle 7 is configured to flex when sharp end 22 of needle 7 withdraws through friction fit needle aperture 12 into fluid receiving cavity 100, whereby sharp end 22 of retractable needle 7 will fall out of alignment with friction fit needle aperture 12. The flexing of retractable needle 7 prevents retractable needle 7 from returning to a slidably disposed relationship with needle end 20 of barrel 1 after retractable needle 7 is fully withdrawn into the barrel 1.

Because retractable needle 7 is preferably very thin, it will readily deform or crumple within fluid receiving cavity 100 when plunger 15 is depressed to return plunger 15 toward an extended position after sharp end 22 of retractable needle 7 has withdrawn through friction fit needle aperture 12. If necessary, retractable needle 7 can be scored to facilitate bending and breaking of needle 7 within fluid receiving cavity 100 when plunger 15 is depressed toward an extended position after sharp end 22 of needle 7 has withdrawn through friction fit needle aperture 12. For example, retractable needle 7 can be scored 270 degrees at ½ inch intervals to facilitate bending and breaking upon return of the plunger 15 toward an extended position. For most aspiration sized needles, scoring is not expected to be necessary.

As shown in FIGS. 1–6, a preferred embodiment of the invention also has a port 3 on barrel 1. As shown in FIG. 4, port 3 is configured to provide fluid passage from fluid receiving cavity 100 for discharging or dispensing collected aspirated matter 18 from fluid receiving cavity 100 of barrel 1 by depressing plunger 15 such that washer end 16 returns toward needle end 20 of barrel 1. Because the body of needle 7 or needle member 7A is preferably very thin, the body of needle 7 or needle member 7A will easily crumple within syringe barrel 1 without impeding the forward travel of plunger 15. Sharp end 22 of needle 7 is, therefore, safely contained within the barrel 1 of the syringe, where it cannot pierce the skin of an operator, patient, or other person. Although port 3 could be placed at any number of locations along the length of barrel 1, it will preferably be placed proximate needle end 20 of barrel 1, such that maximum discharge of aspirated matter 18 can be achieved through return of washer end 16 of plunger 15 to needle end 20 of barrel 1. Port 3 can be placed proximate needle end 20 by placing port 3 on barrel 1 such that it extends through interior wall 80, as shown in FIGS. 1–6, or by placing port 3 on barrel 1 such that it extends through needle end 20 of barrel 1. Although port 3 is depicted in FIGS. 1–6 as extending outwardly, it could be configured to extend inwardly, or it could be simply a hole in barrel 1. Because the interior diameter of port 3 is significantly greater than self sealing friction fit needle aperture 12, the discharge process will not create sufficient internal pressure to cause leakage of aspirated matter 18 through the friction fit needle aperture 12.

As shown in FIGS. 1–6, a seal means 5 is removably positioned on port 3 for preventing aspirated matter from exiting port 3 during collection or storage of aspirated matter 18 in fluid receiving cavity 100. Seal means 5 can be a cap, such as the screw cap shown in the drawings, or it can be a plug, puncture seal, screw, or the like. With seal means 5 removed from port 3, aspirated matter 18 can be discharged through port 3 by depressing plunger 15 forward. After the discharge or dispensing process is complete, seal means 5 can be replaced on port 3, such that the device is ready for safe disposal.

During discharge of collected fluid or aspirated matter 18, sharp end 22 of retractable needle 7 or needle member 7A may accidentally enter port 3. In order to prevent sharp end 22 from exiting port 3, where it would pose a risk of needle stick, the apparatus is preferably fitted with an needle entry barrier 17. Needle entry barrier 17 is configured to prevent retractable needle 7 or needle member 7A from entering port 3 when plunger 15 is moved toward an extended position to expel aspirated matter 18. Needle entry barrier 17 can be positioned on interior wall 80 of barrel 1, between port 3 and washer end 16 of plunger 15. In order to provide maximum range of motion for plunger 15, and hence maximum discharge or dispensing capability, needle entry barrier 17 is preferably positioned adjacent port 3. Additionally, if port 3 is configured to extend inwardly into fluid receiving cavity 100 from interior wall 80 of barrel 1, port 3 can serve a dual role as both port 3 and needle entry barrier 17.

In operation, the person collecting aspirated matter or fluids will sterilize the skin where the insertion is to be made. Then retractable needle 7 or needle member 7A will be injected into a target tissue, such as a lesion. Next, plunger 15 is retracted, creating a vacuum in the fluid receiving cavity 100. The vacuum, and possibly the fluid's own pressure, will cause fluid and aspirated matter 18 to flow through the needle member 7A into the fluid receiving cavity 100. During the initial retraction, needle 7 and engagement member 7B remain stationary while engagement means 13 of plunger cavity 11 is moved rearward toward engagement end 31 of engagement member 7B. Because of the delayed engagement mechanism of plunger cavity 11, engagement means 13, and engagement end 31, fluid and aspirated matter can be collected without moving needle member 7A within the target tissue. When a sufficient or desired amount of fluid or aspirated matter 18 has been collected, the user retracts plunger 15 until sharp end 22 of needle 7 withdraws through friction fit needle aperture 12 into fluid receiving cavity 100, which will occur prior to or when washer end 16 engages rear travel detente 4, as shown in FIG. 3. By removing seal means 5 from port 3 and depressing plunger 15, the collected fluid or aspirated matter 18 may be dispensed in a controlled fashion through port 3. Sharp end 22 of needle member 7A is contained within fluid receiving cavity 100 during discharge of aspirated matter 18 through port 3, such that sharp end 22 is not exposed to human contact. Once the fluids or aspirated matter 18 have been discharged, the deformation of needle member 7A within fluid receiving cavity 100 prevents the syringe from being reused, and also allows the safety syringe to be disposed of without exposing sharp end 22 to human contact.

The syringe can be provided in a container (not shown), such that the once aspirated matter 18 has been collected, the syringe can be placed back in the container for transport, storage, or disposal. When it is desirable to remove aspirated matter 18 from syringe barrel 1, the syringe is removed from its container.

The needle aspiration safety syringe can be used for many applications, such as amniocentesis, spinal taps, needle biopsies of breast and other tissue, orthopedic applications such as joint fluid removal, or practically any other procedure requiring collection of aspirated matter with a needle aspiration syringe.

Although the present invention has been described in terms of specific embodiments, it is anticipated that alterations and modifications thereof will no doubt become apparent to those skilled in the art. It is therefore intended that the following claims be interpreted as covering all such alterations and modifications as fall within the true spirit and scope of the invention.

I claim:

1. A safety syringe for collecting aspirated matter comprising:

a substantially hollow barrel having a needle end, a plunger end, and an interior wall extending between said plunger end and said needle end;

a plunger slidably disposed within said barrel, said plunger having a thumb end and a washer end, said washer end configured to create a seal between said washer end of said plunger and said interior wall of said barrel, said washer end of said plunger containing a plunger cavity; and a retractable needle slidably disposed within said needle end of said barrel, said needle and said needle end of said barrel further configured to create a seal between said needle and said needle end of said barrel, said needle further comprising a sharp end and an engagement end, said engagement end slidably disposed within said plunger cavity, said engagement end configured to engage said plunger cavity after said plunger cavity is retracted relative to said engagement end, whereby said needle may be retracted by retracting said plunger.

2. A safety syringe according to claim 1, wherein said retractable needle is sized to allow said retractable needle to be fully withdrawn into said barrel.

3. A safety syringe according to claim 2, wherein said needle end of said barrel is substantially fluid tight when said retractable needle is fully withdrawn into said barrel.

4. A safety syringe according to claim 3, wherein said needle end of said barrel is provided with a friction fit needle aperture, said friction fit needle aperture configured to render said needle end of said barrel substantially fluid tight when said retractable needle is fully withdrawn into said barrel.

5. A safety syringe according to claim 3, wherein said retractable needle is sufficiently flexible to prevent said retractable needle from returning to said slidably disposed relationship with said needle end of said barrel after said retractable needle is fully withdrawn into said barrel.

6. A safety syringe according to claim 5, wherein said retractable needle is configured to deform within said barrel when said plunger is depressed after said retractable needle is fully withdrawn into said barrel.

7. A safety syringe according to claim 6, wherein said retractable needle is scored to facilitate deformation of said retractable needle within said barrel when said plunger is depressed.

8. A safety syringe according to claim 6, wherein said barrel further comprises a port configured to provide fluid passage from said barrel, and a seal means removably positioned on said port.

9. A safety syringe according to claim 8, wherein said seal means is a cap.

10. A safety syringe according to claim 8, further comprising a needle entry barrier on said interior wall of said barrel between said port and said washer end of said plunger.

11. A safety syringe according to claim 10, wherein said needle entry barrier is adjacent said port.

12. A safety syringe according to claim 2, wherein said retractable needle is sufficiently flexible to prevent said retractable needle from returning to said slidably disposed relationship with said needle end of said barrel after said retractable needle is fully withdrawn into said barrel.

13. A safety syringe according to claim 12, wherein said retractable needle is configured to deform within said barrel when said plunger is depressed after said retractable needle is fully withdrawn into said barrel.

14. A safety syringe according to claim 13, wherein said retractable needle is scored to facilitate deformation of said retractable needle within said barrel when said plunger is depressed.

15. A safety syringe according to claim 13, wherein said barrel further comprises a port configured to provide fluid passage from said barrel, and a seal means removably positioned on said port.

16. A safety syringe according to claim 15, wherein said seal means is a cap.

17. A safety syringe according to claim 15, further comprising a needle entry barrier on said interior wall of said barrel between said port and said washer end of said plunger.

18. A safety syringe according to claim 17, wherein said needle entry barrier is adjacent said port.

19. A safety syringe according to claim 2, wherein said retractable needle is configured to deform within said barrel when said plunger is depressed after said retractable needle is fully withdrawn into said barrel.

20. A safety syringe according to claim 19, wherein said retractable needle is scored to facilitate deformation of said retractable needle within said barrel when said plunger is depressed.

21. A safety syringe according to claim 19, wherein said barrel further comprises a port configured to provide fluid passage from said barrel, and a seal means removably positioned on said port.

22. A safety syringe according to claim 21, wherein said seal means is a cap.

23. A safety syringe according to claim 21, further comprising a needle entry barrier on said interior wall of said barrel between said port and said washer end of said plunger.

24. A safety syringe according to claim 23, wherein said needle entry barrier is adjacent said port.

25. A safety syringe according to claim 2, wherein said barrel further comprises a port configured to provide fluid passage from said barrel, and a seal means removably positioned on said port.

26. A safety syringe according to claim 25, wherein said seal means is a cap.

27. A safety syringe according to claim 25, further comprising a needle entry barrier on said interior wall of said barrel between said port and said washer end of said plunger.

28. A safety syringe according to claim 27, wherein said needle entry barrier is adjacent said port.

29. A safety syringe according to claim 2, wherein said retractable needle has a pivot between said sharp end and said engagement end, said sharp end of said retractable needle pivoting about said pivot when said retractable needle is fully withdrawn into said barrel.

30. A safety syringe according to claim 29, wherein said retractable needle is configured to deform within said barrel when said plunger is depressed after said retractable needle is fully withdrawn into said barrel.

31. A safety syringe according to claim 29, wherein said retractable needle is configured to deform between said sharp end and said pivot when said plunger is depressed after said retractable needle is fully withdrawn into said barrel.

32. A safety syringe according to claim 29, wherein said retractable needle is configured to deform between said engagement end and said pivot when said plunger is depressed after said retractable needle is fully withdrawn into said barrel.

33. A safety syringe according to claim 30, wherein said barrel further comprises a port configured to provide fluid passage from said barrel, and a seal means removably positioned on said port.

34. A safety syringe according to claim 33, wherein said seal means is a cap.

35. A safety syringe according to claim 33, further comprising a needle entry barrier on said interior wall of said barrel between said port and said washer end of said plunger.

36. A safety syringe according to claim 35, wherein said needle entry barrier is adjacent said port.

37. A safety syringe according to claim 3, wherein said retractable needle is configured to deform within said barrel when said plunger is depressed after said retractable needle is fully withdrawn into said barrel.

38. A safety syringe according to claim 37, wherein said retractable needle is scored to facilitate deformation of said retractable needle within said barrel when said plunger is depressed.

39. A safety syringe according to claim 37, wherein said barrel further comprises a port configured to provide fluid passage from said barrel, and a seal means removably positioned on said port.

40. A safety syringe according to claim 39, wherein said seal means is a cap.

41. A safety syringe according to claim 39, further comprising a needle entry barrier on said interior wall of said barrel between said port and said washer end of said plunger.

42. A safety syringe according to claim 41, wherein said needle entry barrier is adjacent said port.

43. A safety syringe according to claim 3, wherein said barrel further comprises a port configured to provide fluid passage from said barrel, and a seal means removably positioned on said port.

44. A safety syringe according to claim 43, wherein said seal means is a cap.

45. A safety syringe according to claim 43, further comprising a needle entry barrier on said interior wall of said barrel between said port and said washer end of said plunger.

46. A safety syringe according to claim 45, wherein said needle entry barrier is adjacent said port.

47. A safety syringe according to claim 3, wherein said retractable needle has a pivot between said sharp end and said engagement end, said sharp end of said retractable needle pivoting about said pivot when said retractable needle is fully withdrawn into said barrel.

48. A safety syringe according to claim 47, wherein said retractable needle is configured to deform within said barrel when said plunger is depressed after said retractable needle is fully withdrawn into said barrel.

49. A safety syringe according to claim 47, wherein said retractable needle is configured to deform between said sharp end and said pivot when said plunger is depressed after said retractable needle is fully withdrawn into said barrel.

50. A safety syringe according to claim 47, wherein said retractable needle is configured to deform between said engagement end and said pivot when said plunger is depressed after said retractable needle is fully withdrawn into said barrel.

51. A safety syringe according to claim 48, wherein said barrel further comprises a port configured to provide fluid passage from said barrel, and a seal means removably positioned on said port.

52. A safety syringe according to claim 51, wherein said seal means is a cap.

53. A safety syringe according to claim 51, further comprising a needle entry barrier on said interior wall of said barrel between said port and said washer end of said plunger.

54. A safety syringe according to claim 53, wherein said needle entry barrier is adjacent said port.

55. A safety syringe according to claim 1, wherein said retractable needle is from about 25 to about 30 gauge.

56. A safety syringe according to claim 1, further comprising a rear travel detente on said interior wall of said plunger end.

57. A safety syringe for collecting aspirated matter comprising:
- a substantially hollow barrel having a needle end, a plunger end, and an interior wall extending between said plunger end and said needle end;
- a plunger slidably disposed within said barrel, said plunger having a thumb end and a washer end, said washer end configured to create a seal between said washer end of said plunger and said interior wall of said barrel;
- a retractable needle slidably disposed within said needle end of said barrel, said needle and said needle end of said barrel further configured to create a seal between said needle and said needle end of said barrel, said needle functionally attached to said plunger,
    - said retractable needle sized to allow said needle to be fully withdrawn into said barrel by retraction of said plunger; and
    - said retractable needle having a pivot between said sharp end and said engagement end, said sharp end of said retractable needle pivoting about said pivot when said retractable needle is fully withdrawn into said barrel.

58. A safety syringe according to claim 57, wherein said retractable needle is configured to deform within said barrel when said plunger is depressed after said retractable needle is fully withdrawn into said barrel.

59. A safety syringe according to claim 58, wherein said barrel further comprises a port configured to provide fluid passage from said barrel, and a seal means removably positioned on said port.

60. A safety syringe according to claim 59, wherein said seal means is a cap.

61. A safety syringe according to claim 59, further comprising a needle entry barrier on said interior wall of said barrel between said port and said washer end of said plunger.

62. A safety syringe according to claim 61, wherein said needle entry barrier is adjacent said port.

63. A safety syringe for collecting aspirated matter comprising:
- a substantially hollow barrel having a needle end, a plunger end, and an interior wall extending between said plunger end and said needle end;
- a plunger slidably disposed within said barrel, said plunger having a thumb end and a washer end, said washer end configured to create a seal between said washer end of said plunger and said interior wall of said barrel; and
- a retractable needle slidably disposed within said needle end of said barrel, said needle and said needle end of said barrel further configured to create a seal between said needle and said needle end of said barrel, said needle functionally attached to said plunger,
    - said retractable needle sized to allow said needle to be fully withdrawn into said barrel by retraction of said plunger,
    - said needle end of said barrel being substantially fluid tight when said retractable needle is fully withdrawn into said barrel, and
    - said retractable needle having a pivot between said sharp end and said engagement end, said sharp end of said retractable needle pivoting about said pivot when said retractable needle is fully withdrawn into said barrel.

64. A safety syringe according to claim 63, wherein said retractable needle is configured to deform within said barrel when said plunger is depressed after said retractable needle is fully withdrawn into said barrel.

65. A safety syringe according to claim 64, wherein said barrel further comprises a port configured to provide fluid passage from said barrel, and a seal means removably positioned on said port.

66. A safety syringe according to claim 65, wherein said seal means is a cap.

67. A safety syringe according to claim 65, further comprising a needle entry barrier on said interior wall of said barrel between said port and said washer end of said plunger.

68. A safety syringe according to claim 67, wherein said needle entry barrier is adjacent said port.

69. A device according to claim 57, wherein said retractable needle is sufficiently flexible to prevent said retractable needle from returning to said slidably disposed relationship with said needle end of said barrel after said retractable needle is fully withdrawn into said barrel.

70. A safety syringe according to claim 69, wherein said retractable needle is configured to deform within said barrel when said plunger is depressed after said retractable needle is fully withdrawn into said barrel.

71. A safety syringe according to claim 70, wherein said retractable needle is scored to facilitate deformation of said needle within said barrel when said plunger is depressed.

72. A safety syringe according to claim 70, wherein said barrel further comprises a port configured to provide fluid passage from said barrel, and a seal means removably positioned on said port.

73. A safety syringe according to claim 72, wherein said seal means is a cap.

74. A safety syringe according to claim 72, further comprising a needle entry barrier on said interior wall of said barrel between said port and said washer end of said plunger.

75. A safety syringe according to claim 74, wherein said needle entry barrier is adjacent said port.

76. A safety syringe according to claim 57, wherein said retractable needle is sufficiently flexible to prevent said retractable needle from returning to said slidably disposed relationship with said needle end of said barrel after said retractable needle is fully withdrawn into said barrel.

77. A safety syringe according to claim 76, wherein said retractable needle is configured to deform within said barrel when said plunger is depressed after said retractable needle is fully withdrawn into said barrel.

78. A safety syringe according to claim 77, wherein said retractable needle is scored to facilitate deformation of said retractable needle within said barrel when said plunger is depressed.

79. A safety syringe according to claim 77, wherein said barrel further comprises a port configured to provide fluid passage from said barrel, and a seal means removably positioned on said port.

80. A safety syringe according to claim 61, wherein said seal means is a cap.

81. A safety syringe according to claim 61, further comprising a needle entry barrier on said interior wall of said barrel between said port and said washer end of said plunger.

82. A safety syringe according to claim 81, wherein said needle entry barrier is adjacent said port.

* * * * *